United States Patent [19]

Ishikawa

[11] 4,050,150

[45] Sept. 27, 1977

[54] MEDICAL NEEDLE HOLDER ASSEMBLY AND METHOD OF AND APPARATUS FOR MANUFACTURING MEDICAL NEEDLE HOLDING ASSEMBLY

[76] Inventor: Soji Ishikawa, No.85, 1 chome, Kamata, Setagaya, Tokyo, Japan

[21] Appl. No.: 730,251

[22] Filed: Oct. 6, 1976

Related U.S. Application Data

[62] Division of Ser. No. 602,740, Aug. 7, 1975, Pat. No. 4,001,929.

[51] Int. Cl.$^2$ .............................................. B23P 19/04
[52] U.S. Cl. .......................................... 29/777; 29/809
[58] Field of Search ........................... 29/771, 777, 809

[56] References Cited

U.S. PATENT DOCUMENTS

| | | | |
|---|---|---|---|
| 2,433,271 | 12/1947 | Grant | 29/446 X |
| 2,581,561 | 1/1952 | Shaw | 29/446 X |
| 2,698,478 | 1/1955 | Heisterkamp et al. | 29/777 |
| 3,133,849 | 5/1964 | Zenick | 29/777 X |
| 3,270,483 | 9/1966 | Smoyer et al. | 29/777 X |
| 3,501,826 | 3/1970 | Marcus | 29/809 X |
| 3,689,984 | 9/1972 | Biederman et al. | 29/809 X |
| 3,973,313 | 8/1976 | Hunter | 29/429 X |

Primary Examiner—Charlie T. Moon
Attorney, Agent, or Firm—Haseltine, Lake & Waters

[57] ABSTRACT

An apparatus for forming medical needle holder assembly employing a generally tubular needle holder, a filter element constituted by a wad of a lengthy filament yarn of snythetic resin and a generally tubular filter retainer adapted to be received in the needle holder with the filter element fitted in the needle holder. The needle holder assembly is completed by holding the needle holder and the filter retainer in positions longitudinally aligned with each other, positioning a predetermined length of filament yarn between the needle holder and the filter retainer, producing a unidirectional stream of air flowing away from the filament yarn thus positioned toward the foremost end of the filter retainer for moving the filament yarn onto the foremost end of the filter retainer, and moving the combination of the filter retainer and the filament yarn toward the needle holder, and forcing the filter retainer into the needle holder so that the filament yarn which has been in a loosely tangled condition is compacted into wad form within the needle holder.

11 Claims, 8 Drawing Figures

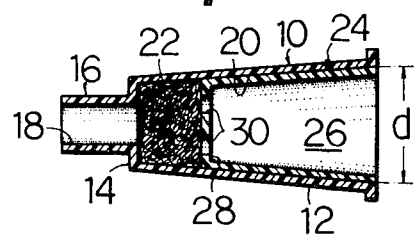
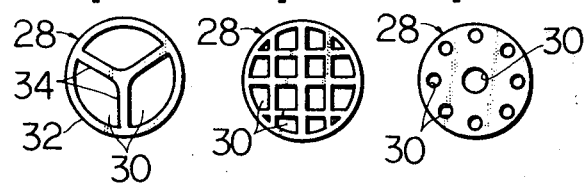
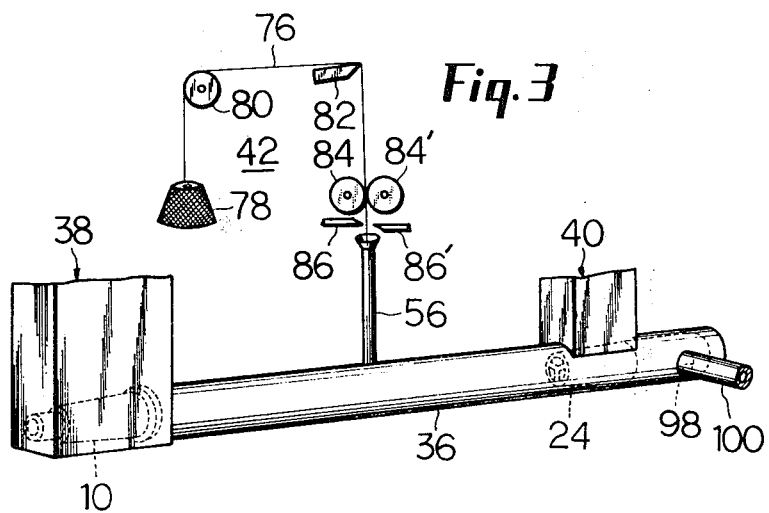

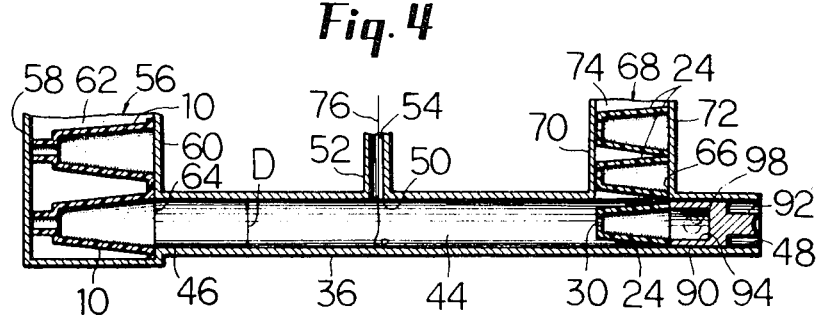
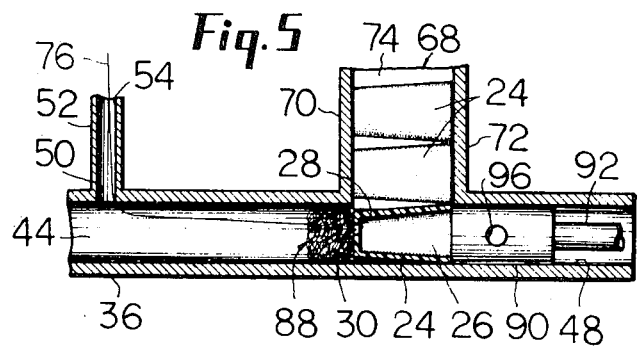
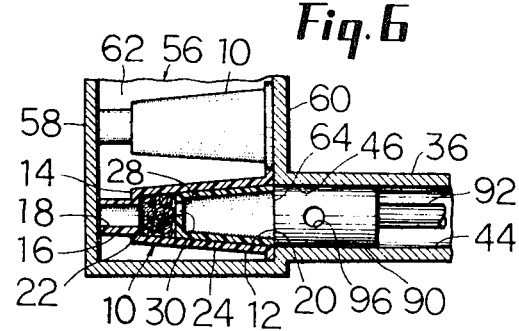

MEDICAL NEEDLE HOLDER ASSEMBLY AND METHOD OF AND APPARATUS FOR MANUFACTURING MEDICAL NEEDLE HOLDING ASSEMBLY

This is a division of application ser. No. 602,740 filed Aug. 7, 1975, now U.S. Pat. No. 4,001,929.

BACKGROUND OF THE INVENTION

The present invention relates to a needle holder assembly for use with a medical administering device or appliance such as a hypodermic syringe or a venoclysis equipment for introducing a liquid medicament or transfusing blood into human body.

Extreme precautions are taken to prevent a pharmaceutical preparation or blood for transfusion from becoming contaminated with impurities before the preparation or blood is injected into the human body. Actually, however, there still exist various possibilities that impurities are present in or admixed to the preparation or blood before and even during the administering process. Impurities may happen to be introduced into a liquid medicament when, for example, an ampoule or other breakable container storing the preparation is punctured prior to injection or when a fluid conducting tube is being fitted to the rubber plug of the reservoir of a venoclysis equipment. The fine fragments of the punctured container or the fine particles of rubber scrapped off from the plug of the venoclysis equipment may find their way through the administering system into the blood stream of the human body and may thus injure the vascular tissues.

A variety of filter media have therefore been developed and have found practical applications for the purpose of removing impurities from liquid medicaments and blood for transfusion before the medicaments or blood are discharged from the needles of canulae of the administering devices. One of the typical examples of the prior art filter media adapted to achieve this purpose if formed of staple fibers which are pressed or otherwise compacted into lump form and another example if formed of nylon fabrics or a mass of sintered nylon powder. The filter element is usually fitted into the passageway in the needle holder and collects impurities when the liquid medicament or blood for transfusion is passed through the filter element toward the needle. When the filter element is thus subjected to the stream of the medicament of blood passing therethrough, it frequently happens that relatively short fibers or the fragments of fibers are separated from the lump of the compacted staple fibers or the fabrics of nylon or fine gragments are fractured or torn apart from the mass of the sintered nylon powder. This not only results in deterioration of the collection efficiency of the filter element being used but is causative of production of additional impurities (herein called "secondary impurities") although the majority of the impurities (herein called "primary impurities") initially contained in the medicament or blood directed into the needle holder may be collected by the filter element. The filter element thus provides in itself another source of impurities and loses in significance as the filter means.

With a view to solving these problems, I, the inventor, have proposed a new filter element in a medical needle assembly as disclosed in U.S. Pat. No. 3,859,999 dated Jan. 14, 1975 and assigned to Ishikawa Manufacturing Company, Limited, Tokyo, Japan. The filter element shown in this issued patent comprises a wad of at least one length of continuous filament of synthetic resin substantially uniformly entwined into wad form and is preferably located at the foremost end of the longitudinal passageway in a needle holder. In the course of the manufacture of such needle assemblies on a commercial basis, however, it has been found that difficulties are encountered in accurately locating the filter element in the needle holder and fixedly holding the filter element in position within the needle holder. This is partly because of the extremely small space available in the needle holder and partly because of the inherently shapeless configuration of the filter element composed of the wad of an entwined filament. If the filter element is located off of a predetermined position relative to the needle holder or dislodged from the predetermined position, the filter element causes obstruction when the needle assembly is being fitted to a syringe barrel or an adapter of a venoclysis equipment. The present invention contemplates provision of a medical needle holder assembly which is free from such a problem encountered in the applicant's previously proposed needle assembly as well as the problems inherent in needle holder assemblies using other prior art filter elements of the natures hereinbefore described.

SUMMARY OF THE INVENTION

It is, therefore, an important object of the present invention to provide an improved medical needle holder assembly having a filter element which is capable of removing impurities, viz., primary impurities from a liquid medicament or blood to be discharged from the needle holder assembly and which will not form a source of secondary impurities during use.

It is another important object of the invention to provide an improved medical needle holder assembly having a filter element which held in position within the needle holder assembly during transportation, storage and use.

It is still another important object of the present invention to provide a method of assembling together a needle holder, a filter element and a filter retainer so as to obtain such an improved needle holder assembly.

It is still another important object of the invention to provide apparatus adapted to put the method into practice on a commercial basis.

In accordance with one outstanding aspect of the present invention, there is provided a method of assembling together a generally tubular needle holder, a filter element composed of a wad of a predetermined length of filament yarn of synthetic resin and a generally tubular filter retainer adapted to be received in the needle holder with the filter element fitted in the needle holder, comprising (1) feeding the needle holder and the filter element into respective predetermined positions longitudinally spaced apart from and aligned with each other and feeding the filament yarn into a predetermined position intermediate between the predetermined positions of the needle holder and the filter retainer, (2) producing a unidirectional stream of air flowing from the predetermined position of the filament yarn toward the predetermined position of the filter retainer for moving the filament yarn from the predetermined position thereof toward the filter retainer in the predetermined position thereof until the filament yarn is forced in the form of a tangle against the foremost end of the filter retainer, (3) moving the filter retainer from the predetermined position thereof toward the needle holder in the predetermined position thereof with the tangle of the filament yarn carried on the foremost end of the filter retainer, and (4) forcing the filter retainer into the needle holder in the predetermined position thereof so that the tangle of the filament yarn is compacted into wad form within the needle holder. The method may further comprise subjecting the filament yarn to a predetermined tensile pull, scraping the filament yarn against a sharpened edge while applying the tensile pull to the yarn for elastically elongating the yarn, and releasing the filament yarn from the tensile pull for allowing the yarn to longitudinally shrink before the filament yarn is fed into the predetermined position thereof. The respective predetermined positions of the needle holder and the filter retainer are preferably aligned with each other horizontally. The unidirectional stream of air to move the filament yarn onto the foremost end of the filter retainer may be produced preferably by developing a suction behind the filter retainer in the predetermined position thereof so that a differential pressure is created between the predetermined position of the filament yarn and the filter retainer.

In accordance with another outstanding aspect of the present invention, there is provided an apparatus for assembling together the above mentioned needle holder, filter element and filter retainer, comprising (1) an elongated hollow transport tube having a longitudinal passageway which is open at its foremost end and having formed in its intermediate portion an opening which is sized to permit the filament yarn to pass therethrough, (2) first feeding and positioning means for feeding the needle holder in each cycle of operation into a predetermined position longitudinally aligned with the longitudinal passageway in the transport tube and having its rearmost end located at the open foremost end of the longitudinal passageway, (3) second feeding and positioning means for feeding the filter retainer in each cycle of operation into a predetermined position within the longitudinal passageway in the transport tube, the predetermined position of the filter retainer being longitudinally spaced apart and aligned with the predetermined position of the needle holder across the intermediate portion of the longitudinal passageway, (4) third feeding and positioning means for feeding the filament yarn in each cycle of operation into a predetermined position in the intermediate portion of the longitudinal passageway of the transport tube through the opening formed in the intermediate portion, (5) pneumatic transfer means for producing in the longitudinal passageway in the transport tube a unidirectional stream of air flowing from the intermediate portion toward the predetermined position of the filter retainer for moving the filament yarn from the predetermined position thereof toward the filter retainer in the predetermined position thereof until the filter element is forced in the form of a tangle against the foremost end of the filter retainer, and (6) drive means for moving the filter retainer from the predetermined position thereof toward the needle holder in the predetermined position thereof with the tangle of the filament yarn carried on the foremost end of the filter retainer and forcing the filter retainer into the needle holder in the predetermined position thereof so that the tangle of the filament yarn is compacted into wad form within the needle holder.

The needle holder assembly thus obtained in accordance with the present invention comprises, in combination, a generally tubular needle holder having a hollow body portion formed with an annular foremost end wall, a generally tubular filter retainer received in the body portion and having a apertured foremost end wall spaced apart from the annular foremost end wall of the body portion of the needle holder, and a filter element which is composed of a wad of a single lengthy filament yarn of synthetic resin and which is positioned between the annular foremost end wall of the body portion of the needle holder and the apertured foremost end of the filter retainer.

The needle holder assembly and the method of and apparatus for obtaining such a needle holder assembly in accordance with the present invention will become more apparent from the following description taken in conjunction with the accompanying drawings in which:

In the Drawings

FIG. 1 is a longitudinal sectional view of a preferred embodiment of the medical needle holder assembly according to the present invention;

FIGS. 2a, 2b and 2c are plan views each of which shows a preferred example of the pattern of the apertures formed in the foremost end wall of the filter retainer incorporated in the needle holder assembly illustrated in FIG. 1;

FIG. 3 is a perspective view of an arrangement which forms part of a preferred embodiment of the apparatus according to the present invention;

FIG. 4 is a longitudinal sectional view showing part of the arrangement illustrated in FIG. 3 in one stage of operation;

FIG. 5 is a longitudinal sectional view showing, to an enlarged scale, part of the arrangement illustrated in FIG. 3 in another stage of operation; and FIG. 6 is a longitudinal sectional view showing, also to an enlarged scale, part of the arrangement illustrated in FIG. 3 in still another stage of operation.

PREFERRED EMBODIMENT

Referring to FIG. 1, a needle holder assembly embodying the present invention comprises a needle holder 10 which consists of a forwardly tapered hollow body portion 12 having an annular end wall 14 at its reduced foremost end and a cylindrical extension 16 projecting forward from the annular end wall 14 of the body portion 12 and having a longitudinal passageway 18 which is open at the foremost end of the extension 16. The body portion 12 is formed with a generally frusto-conical cavity 20 which is open at the enlarged rearmost end of the body portion 12 and which communicates at the opposite end of the body portion 12 with the longitudinal passageway 18 in the cylindrical extension 16. A filter element 22 composed of a wad of a single lengthy filament yarn of synthetic resin is located in the foremost end portion of the frusto-conical cavity 20 in the body portion 12 of the needle holder 10 thus constructed and is held in position by means of a forwardly tapered hollow filter retainer 24. The filter retainer 24 has a generally frusto-conical outer peripheral surface which is shaped conformingly to part of the inner peripheral surface of the body portion 12 of the needle holder 10. The filter retainer 24 is closely fitted into the main body portion 12 of the needle holder 10 in such a manner that the reduced foremost end thereof is spaced apart a predetermined distance from the inner face of the annular end wall 14 of the body portion 12 in longitudinal direction of the retainer 24 and that the enlarged rearmost end thereof is substantially flush with the enlarged rearmost end of the body portion 12 of the needle holder 10. The outside diameter of the rearmost end of the filter retainer 24 is thus substantially equal to the inside diameter of the rearmost end of the body portion 12 of the needle holder 10, as denoted by $d$ in FIG. 1. The filter retainer 24 has a longitudinal passageway 26 fully open at the enlarged rearmost end of the retainer 24 and has formed at its reduced foremost end an end wall 28 which is formed with a plurality of apertures 30. The apertures 30 are preferably arranged substantially symmetrically with respect to the center axis of the end wall 28 and uniformly distributed in the foremost end wall 28 with a suitable pattern. FIGS. 2a, 2b and 2c illustrate preferred examples of the pattern with which the apertures 30 may be arranged in the end wall 28 of the filter retainer 24. In the arrangement shown in FIG. 2a, the end wall 28 of the filter retainer is made up of a circular rim portion 32 and a plurality of radial portions 34 which are substantially equiangularly spaced apart from each other about the center axis of the end wall 28. The radial portions 34 extend spokewise inwardly from the rim portion 32 and meet each other at the center axis of the end wall 28 so that the individual apertures 30 have generally sectorial forms having substantially equal central angles about the center axis of the end wall 28. The radial portions 34 are herein shown as being three in number so that each of the sectorial apertures 30 is assumed to have a central angle of approximately 120 degrees about the center axis of the end wall 28 but it is apparent that the number of the radial portions 34 may be selected arbitarily depending upon the specific design considerations to be given to the needle assembly. The end wall 28 shown in FIG. 2b is in the form of a grille having a number of interstices which form the apertures 30. These apertures 30 are shown to be formed by crossings intersecting at right angles but, if desired, the crossings may be arranged in such a manner as to intersect each other at other angles insofar as the apertures 30 are distributed approximately uniformly in the end wall 28. In the end wall 28 shown in FIG. 2c, one of the apertures 30 is located substantially centrally of the end wall 28 and the others are arranged around the central aperture preferably symmetrically with respect to the center axis of the end wall 28. The central aperture is shown to be larger in diameter than the others but it is apparent that the respective diameters of the individual apertures 30 arranged as shown in FIG. 2c may be selected arbitarily.

Turning back to FIG. 1, the filter retainer 24 having the apertured foremost end wall 28 thus arranged terminates longitudinally halfway of the frusto-conical cavity 20 in the body portion 12 of the needle holder 10 so that the filter element 20 formed of a wad having an inherently shapeless configuration is stuffed between the inner face of the previously mentioned annular end wall 14 off the body portion 12 of the needle holder 10 and the outer face of the apertured foremost end wall 28 of the filter retainer 24. The relation between the length of the cavity 20 in the body portion 12 of the needle holder 10 and the length of the filter retainer 24, viz., the size of the space to accommodate the filter element 22 should therefore be selected depending upon the desired density or, more exactly, the percent of voidness of the filter element 22.

With the filter element 22 and the filter retainer 24 thus fitted into the needle holder 10, communication is provided between the longitudinal passageway 26 in the filter retainer 24 and the longitudinal passageway 18 in the cylindrical extension 16 of the needle holder 10 through the apertures 30 in the foremost end wall 28 of the filter retainer 24 and the interstices in the filter element 22. A piercing needle is fitted to the cylindrical extension 16 of the needle holder 10 as is customary in the art whilst the filter retainer 24 is fitted to the syringe barrel of a hypodermic syringe or to the adapter of a venoclysis equipment, though not shown in the drawings.

Similarly to the filter medium incorporated into the medical needle assembly disclosed in the previously named U.S. Pat. No. 3,859,999, the filament yarn constituting the filter element 22 of the needle holder assembly embodying the present invention preferably has a denier number within the range of from about 75 to about 150 or, more preferably, from about 75 to about 85 and is stuffed into the needle holder 10 to form a wad which preferably has a density within the range of from about 0.8 gram/cm$^3$ to about 1.6 gram/cm$^3$ or, more preferably, from about 0.8 gram/cm$^3$ to about 0.9 gram/cm$^3$. Such a filament yarn may be either a monofilament yarn composed of a single lengthy filament or a multifilament yarn composed of a plurality of spun lengthy filaments. In either case, the filament or each of the filaments should be produced by extruding a continuous filament from an orifice in a plastics extrusion die (not shown) which is well known in the art and cutting the continuous filament to a predetermined length after the extruded filament is set. The filament produced in this manner is devoid of and free from the possibility of forming short fibers and, for this reason, there is not any fear that the filter element 22 constituted by such a filament or filaments should produce secondary impurities in the dosage solution or blood which is passed through the filter element during use of the needle assembly. For the reason which will be clarified later, furthermore, a multifilament yarn is preferable to a monofilament yarn as the material to form the filter element 22.

FIG. 3 illustrates an arrangement forming part of a preferred embodiment of an apparatus according to the present invention adapted to easily and accurately assemble together the needle holder 10, the filter element 22 and the filter retainer 24 of the natures thus far described with reference to FIG. 1.

The arrangement shown in FIG. 3 comprises an elongated, horizontal hollow transport tube 36 and first, second and third feeding and positioning means 38, 40 and 42 which are respectively operative to convey the above mentioned needle holder, filter retainer and filament yarn into predetermined positions relative to the transport tube 36 in each cycle of operation. As is better seen in FIG. 4, the transport tube 36 is formed with a longitudinal passageway 44 extending throughout the length of the tube 36 and having open foremost and rearmost ends 46 and 48. The transport tube 36 is further formed with an opening 50 in the top wall of its intermediate portion for the purpose of admitting a filament yarn into the tube 36 as will be described later. The transport tube 36 is preferably provided with a guide tube 52 having a passageway 54 extending upwardly from the above mentioned opening 50 in the transport tube 36 and terminating at the upper end of the guide tube 52.

In the vicinity of the foremost end of the transport tube 36 thus arranged is located a magazine 56 which forms part of the above mentioned first feeding and positioning means 38. As will be better seen from FIG. 4, the magazine 56 has front and rear vertical walls 58 and 60 so as to form therebetween a vertical chamber 62 which is generally perpendicular to the direction in which the transport tube 36 extends. The magazine 56 has a circular opening 64 formed in a lower end portion of its rear vertical wall 60 and the transport tube 36 has its foremost and fixedly connected to or, as shown, innegral with the rear vertical wall 60 of the magazine 56 so that the longitudinal passageway 44 in the transport tube 36 has its foremost open end 46 contiguous to the lowermost portion of the vertical chamber 62 through the opening 64 in the rear vertical wall 60 of the magazine 56. The magazine 56 thus constructed is adapted to have accomodated in the vertical chamber 62 thereof a stack of needle holders 10 each having the configuration illustrated in FIG. 1. The needle holders 10 are stacked upon one another in vertical direction within the vertical chamber 62 so that the one located at the vertical chamber 62 is substantially in line with the longitudinal passageway 44 in the transport tube 36 and has its open rearmost end located in close proximity to the circular opening 64 in the rear vertical wall 60 of the magazine 56. The front and rear vertical walls 58 and 60 of the magazine 56 are spaced apart a distance which is substantially equal to the overall length of the needle holders 10 thus positioned within the chamber 62 so that each of the needle holders 10 above the one located at the bottom of the vertical chamber 62 of the magazine 56 has its foremost and rearmost ends in slidable contact with the inner faces of the front and rear vertical walls 58 and 60, respectively. The circular opening 64 in the rear vertical wall 60 of the magazine 56 has a diameter which is substantially equal to the inside diameter of the transport tube 36 as denoted by D in FIG. 4. The diameter D is substantially equal to the inside diameter $d$ of the enlarged open rearmost end of each needle holder 10. The needle holder 10 located at the bottom of the vertical chamber 62 therefore has its rearmost end in contact with the circular edge portion of the rear vertical wall 60 formed with the opening 64 and its foremost end in contact with the inner face of the front vertical wall 58 of the magazine 56.

Though not shown, the first feeding and positioning means of the apparatus embodying the present invention further comprise a holder feed mechanism operative in predetermined cycles to downwardly convey the needle holders 10 within the vertical chamber 62 in the magazine 56 successively into the bottom portion of the chamber 62, vix., a position aligned with the longitudinal passageway 44 in the transport tube 36 through the circular opening 64 in the rear vertical wall 60 of the magazine 56 and to withdraw completed needle holder assemblies successively from the bottom portion of the chamber 62. The construction of such a mechanism is a mere matter of design choice and is not herein illustrated.

As is also seen in FIG. 4 the transport tube 36 further has an opening 66 formed in the top wall of its portion in the neighbourhood of the rearmost end thereof and carried on the particular portion a magazine 68 which forms part of the second feeding and positioning means 40 previously mentioned with respect to the arrangement illustrated in FIG. 3. The magazine 68 has front and rear vertical walls 70 and 72 which are spaced apart in parallel from each other so as to form therebetween a vertical chamber 74. The front and rear vertical walls 70 and 72 have their respective lower ends fixedly connected to or, as shown, integral with the top wall of the transport tube 36 so that the vertical chamber 74 in the magazine 68 is open at its lower end to the longitudinal passageway 44 in the transport tube 36 through the opening 66. The magazine 68 thus constructed is adapted to have accommodated within the vertical chamber 74 thereof a stack of filter retainers 24 each having the configuration illustrated in FIG. 1. The filter retainers 24 are stacked upon one another in vertical direction within the chamber 74 so that the lowermost one of the filter retainers is positioned within the longitudinal passageway 44 in the transport tube 36 with its reduced foremost end directed toward the foremost end 46 of the passageway 44 and its enlarged rearmost end located at a predetermined distance from the rearmost end of the passageway 44 as shown. Since, in this instance, the outside diameter $d$ of the enlarged rearmost end of each filter retainer 24 is substantially equal to the inside diameter D of the transport tube 36 as will be understood from the foregoing description, the filter retainer 24 positioned in the transport tube 36 is longitudinally slidable in the passageway 44 in the transport tube 36. Though not shown in the drawings, the second feeding and positioning means of the apparatus embodying the present invention further comprises a retainer feed mechanism operative to downwardly move the filter retainers 24 successively into the longitudinal passageway 44 in the transport tube 36 in predetermined cycles which are substantially synchronized with the cycles in which the needle holders 10 in the magazine 56 of the first feeding and positioning means are moved downwardly in the vertical chamber 62 of the magazine 56. The construction of such a mechanism is merely a matter of design choice for those skilled in the art and is not herein shown, as in the case of the holder feed mechanism forming part of the first feeding and positioning means.

Turning back to FIG. 3, the third feeding and positioning means 42 of the apparatus according to the present invention is intended to feed a continuous filament yarn 76 from any suitable source such as a yarn package 78 supported on a creel (not shown). If desired, the filament yarn 76 may be supplied directly from an extrusion die producing a monofilament or a spinning process producing a multifilament yarn, though not shown in the drawings. The yarn 76 from whatever source is supplied, is passed through a tensioning roller 80 to a stationary knife-edged member 82 serving as scraping means for the yarn 76 as will be described in details. The knife-edged member 82 has a sharpened horizontal edge which is preferably located over the upper end of the previously described guide tube 52 on the transport tube 36 as shown. Below the knife-edged member 82 are positioned a pair of feed rollers 84 and 84' which are in rolling contact with each other over the upper end of the above mentioned guide tube 52. One of the feed rollers 84 and 84' is driven for rotation about its axis by suitable drive means such as an electric motor (not shown) so that the filament yarn 76 from the supply package 78 is continuously passed between the feed rollers 84 and 84' at a predetermined rate and is inserted into the vertical passageway 54 in the guide tube 52. Immediately above the upper end of the guide tube 52 are positioned suitable cutting means such as for example a pair of knives 86 and 86'. The kinves 86 and 86' are operatively connected to suitable actuating means (not shown) adapted to measure the length of the filament yarn 76 passed between the feed rollers 84 and 84' or admitted into the guide tube 52 and to actuate the knives 86 and 86' cut the yarn 76 in a predetermined length during each of cycles which are synchronized with the cycles in which the needle holders 10 in the magazine 56 of the first feeding and positioning means and the filter retainers 24 in the magazine 68 of the second feeding and positioning means are successively moved into respective positions aligned with each other through the longitudinal passageway 44 in the transport tube 36 (see FIG. 4). A segment of filament yarn with the predetermined length is in this manner inserted into the guide tube 52 in each cycle of operation. As illustrated in FIG. 4, the segment of the filament yarn 76 thus inserted into the guide tube 52 collects in the longitudinal passageway 44 in the transport tube 36 below the opening 50 by reason of the gravity thereof and is loosely entwined into the form of a tangle 88. The tangle 88 of the filament yarn is temporarily detained in the intermediate portion of the longitudinal passageway 44 in the transport tube 36. The guide tube 52 is herein assumed to form part of the third feeding and positioning means although such a tube may be dispensed with if desired.

A cylindrical piston 90 is longitudinally slidable through the longitudinal passageway 44 in the transport tube 36 between a first position having its foremost end substantially flush with the inner face of the rear vertical wall 72 of the magazine 68 as seen in FIGS. 4 and 5 and a second position having the foremost end located at the foremost end 46 of the longitudinal passageway 44 as seen in FIG. 6. The piston 90 has its rearmost end fixedly connected to or, as shown, integral with a connecting rod 92 which is in turn connected to a suitable mechanical driving source (not shown). The driving source is adapted to move the piston 90 forwardly from the first position to the second position thereof and thereafter backwardly from the second position to the first position thereof during each of the cycles of operation. The piston 90 is formed with a cylindrical cavity 94 which is open at the foremost end of the piston 90 and closed at the rearmost end of the piston 90. The piston 90 has further formed in its peripheral wall an aperture 96 (FIGS. 5 and 6) which is open to the cavity 94. In consonance with the aperture 96 thus provided in the piston 90, the transport tube 36 is formed with a vent 98 (shown by dotted lines in FIGS. 3 and 4) which is so located as to be in alignment with the aperture 96 in the piston 90 when the piston 90 is in the previously mentioned first position thereof as seen in FIGS. 4 and 5. The vent in the transport tube 36 is in communcation with a source (not shown) of suction or a partial vacuum by way of a suction pipe 100 connected to the transport tube 36 as illustrated in FIG. 3. When the piston 90 is in the first position thereof and simultaneously the filter retainer 24 is positioned within the transport tube 39 with its rearmost end engaged by the foremost end of the piston 90 as seen in FIGS. 4 and 5, communication is established between the longitudinal passageway 44 in the transport tube 36 and the source of suction through the apertures 30 in the foremost end wall 28 of the filter retainer 24, the longitudinal passageway 26 in the filter retainer 24, the cavity 94 and the aperture 96 in the piston 90, the vent 98 in the transport tube 36 and the passageway (not shown) in the suction pipe 98. When a suction is thus developed in the transport tube 36 with the upper end of the guide tube 52 open to the atmosphere, there is created a differential pressure between the intermediate portion of the longitudinal passageway 44 and the vent 98 in the transport tube 36 so that a unidirectional stream of air is produced away from the intermediate portion of the longitudinal passageway 44 toward the foremost end of the filter retainer 24 positioned ahead of the piston 90. As an alternative to the suction thus built up in the transport tube 36, air under pressure may be ejected into the longitudinal passageway 44 in the transport tube 36 in a direction reverse to the direction of the suction so as to produce an essentially similar stream of air in the passageway 44.

The operation of the apparatus thus constructed and arranged will not be described with concurrent reference to FIGS. 3 to 6. Throughout the period of operation, one of the feed rollers 84 and 84' (FIG. 3) is kept driven by suitable drive means (not shown) so that the filament yarn 76 is continuously fed from the yarn package 78 at a fixed rate through the tensioning roller 80 and the stationary knife-edged member 82 and is subjected to a tensile pull which is maintained substantially constant by means of the tensioning roller 80. When the filament yarn 76 is passed through the knife-edged member 82, the yarn 76 is scraped against the sharpened horizontal edge of the knife-edged member 82 and, as a consequence, the filament or each of the filaments of synthetic resin constituting the yarn 76 is elastically elongated or drawn because the yarn 76 is maintained taut between the knife-edged member 82 and the feed rollers 84 and 84' by means of the tensioning roller 80 which is positioned between the yarn package 78 and the knife-edged member 80. It is, in this instance, important that the tensioning roller 80 be so conditioned as not to produce an overstrain in the filament yarn 76 for the purpose of preventing the filament yarn 76 from being cut at the sharpened edge of the knife-edge member 82 or between the knife-edged member 82 and the feed rollers 84 and 84'. When the filament yarn 76 which is elastically elongated or drawn in this fashion is freed from the tension at a subsequent stage of process, the yarn 76 is allowed to shrink longitudinally and becomes curled throughout its length with the result that the yarn 76 intricately entwined on itself and to form a uniformly dense filter element at a further subsequent stage. To enable the knife-edged member 82 to effectively scrape the filament yarn 76, it is advisable that the sharpened horizontal edge of the knife-edged member 82 be located vertically in alignment with the upper end of the guide tube 52 on the horizontal transport tube 36 as previously noted.

The filament yarn 76 which has passed through the feed rollers 84 and 84' is downwardly fed and inserted into the vertical passageway 54 in the guide tube 52. When the filament yarn 76 thus admitted into the guide tube 52 reaches a predetermined length, the knives 86 and 86' positioned in proximity to the upper end of the guide tube 52 are actuated to cut the yarn 76 into a segment having the predetermined length. The segment of the filament yarn 76 falls through the vertical passageway 54 in the guide tube 52 and collects within the intermediate portion of the longitudinal passageway 44 in the horizontal transport tube 36 as seen in FIG. 4. The segment of the filament yarn, which is now longitudinally shrunk and curled as above noted, is temporarily detained loosely entwined into the form of a tangle 88 and is within the intermediate portion of the longitudinal passageway 44 in the transport tube 36. The knives 86 and 86' are actuated in predetermined cycles so that the segment of the filament yarn having the predetermined length is supplied to the transport tube 36 in each of the cycles.

While the segment of the filament yarn 76 is thus being fed into the transport tube 36 by the third feeding and positioning means 38 in each cycle of operation, the holder feed mechanism forming part of the first feeding and positioning means 38 and the retainer feed mechanism forming part of the second feeding and positioning means 40 are initiated, either concurrently or at different timings, into action to downwardly move the needle holders 10 within the vertical chamber 62 in the magazine 56 and to downwardly move the filter retainers 24 in the vertical chamber 74 of the magazine 68. The lowermost one of the stack of needle holders 10 within the vertical chamber 62 in the magazine 56 is thus positioned at the bottom of the chamber 62 and is thus aligned with the longitudinal passageway 44 in the transport tube 36 and the lowermost one of the filter retainers 24 in the vertical chamber 74 of the magazine 68 is fed into the longitudinal passageway 44 in the transport tube 36 and is aligned with the needle holder 10 positioned ahead of the foremost end 46 of the longitudinal passageway 44, as seen in FIG. 4. When the lowermost one of the stack of the filter retainers 24 is positioned in the longitudinal passageway 44 in the transport tube 36, the piston 90 is held in its first position having the foremost end in contact with the enlarged open rearmost end of the particular filter retainer 25 and having the aperture 96 aligned with the vent 98 in the transport tube 36 as will be seen from FIGS. 4 and 5. A suction is then developed in the passageway in the suction pipe 100 (FIG. 3) so that a unidirectional stream of air is produced in the longitudinal passageway 44 in the transport tube 36. The stream of air flows from the intermediate portion of the passageway 44 toward the piston 90 being the filter retainer 24 in the passageway 24 and urges the tangle 88 of the filament yarn toward the filter retainer 24 in the passageway 44. The tangle 88 of the filament yarn is consequently moved onto the foremost end of the filter retainer 24 in the passageway 44 and is forced against the outer face of the apertured foremost end wall 28 of the particular filter retainer 24 as seen in FIG. 5. The stream of air past the interstices in the tangle 88 of the filament yarn thus forced against the forward end face of the filter retainer 24 is directed into the suction pipe 100 through the apertures 30 in the foremost end wall 28 and the longitudinal passageway 26 of the filter retainer 24, the cavity 94 and the aperture 96 in the piston 90 and the vent 98 in the transport tube 36 in this sequence. When the tangle 88 of the filament yarn reached the foremost end of the filter retainer 24 in the longitudinal passageway 44 in the transport tube 36, then the supply of suction is interrupted and, in turn, the drive means for the piston 90 is actuated to move the piston 90 forwardly in the longitudinal passageway 44 from its first position illustrated in FIG. 5. As the piton 90 is thus moved forward from the first position thereof, the filter retainer 24 contacting the foremost end of the piston 90 and the tangle 88 of the filament yarn contacting the foremost end face of the retainer element 24 are also moved forward in the longitudinal passageway 44 in the transport tube 36. When the piston 90 reaches its second position having the foremost end located at the foremost end 46 of the longitudinal passageway 44, the filter retainer 24 is positioned immediately ahead of the foremost end 46 of the passageway 44 in the transport tube 36 and is received into the body portion 12 of the needle holder 10 positioned at the bottom of the vertical chamber 62 in the magazine 56 as seen in FIG. 6. The filter retainer 24 thus fitted to the needle holder 10 has it foremost end wall 28 spaced apart from the annular end wall 14 of the body portion 12 of the needle holder 10 so that the tangle 88 of the filament yarn at the foremost end of the filter retainer 24 is received between the outer face of the apertured foremost end wall 28 of the filter retainer 24 and the inner face of the annular end wall 14 of the main body portion 12 of the needle holder 10. The tangle 88 of the filament yarn is consequently compacted into the form of a wad constituting a filter 22. When the filter retainer 24 is forced into the body portion 12 of the needle holder 10, the needle holder 10 is forced at the foremost end of its cylindrical extension 16 against the inner face of the front vertical wall 58 of the magazine 56 and is securely held in position relative to the magazine so that the filter retainer 24 can be closely and accurately fitted to the needle holder 10. A needle assembly is now complete with the needle holder 10 and the filter retainer 24 fitted to each other with the filter element 22 held in position within the longitudinal passageway 20 of the needle holder 10 as is better seen in FIG. 1. The holder feed mechanism forming part of the first feeding and positioning means 38 (FIG. 3) is then actuated to withdraw the complete needle assembly from the chamber 62 in the magazine 56 and to further move the stack of the needle holder 10 downwardly in the chamber 62 so that another needle holder 10 is positioned at the bottom of the chamber 62. On the other hand, the piston 90 is moved back from its second position shown in FIG. 6 to its first position shown in FIG. 5 by the action of the drive means associated with the connecting rod 92 for the piston 90 or by a spring action constantly biasing the connecting rod 92 to move the piston 92 toward the first position thereof. When the piston 90 is thus retracted into its first position close to the rearmost end 48 of the longitudinal passageway 44 in the transport tube 36, then the retainer feed mechanism forming part of the second feeding and positioning means 40 (FIG. 3) is actuated to further move the stack of the filter retainers 24 downwardly in the vertical chamber 74 of the magazine 68 so that another filter retainer 24 is moved into the longitudinal passageway 44 in the transport tube 36. By this time, a second segment of filament yarn is collected in the form of a tangle 88 within the intermediate portion of the transport tube 36 and is ready to be moved onto the foremost end of the filament retainer 24 by a suction to be developed in the suction pipe 100. Medical needle assemblies each having the configuration illustrated in FIG. 1 are in this fashion completed through repetition of the steps thus far described with reference to FIGS. 3 to 6.

From the foregoing description it will be appreciated that the present invention provides the following major advantages:

1. Because of the fact that the filter element 22 is constituted by a single filament yarn of synthetic resin, the filter element 22 will not form a souce of secondary impurities that would otherwise contaminate the liquid medicament or blood which has been cleared of primary impurities. For the same reason, the filtration ability and efficiency of the filter element 22 can be easily and accurately controlled by selecting the length and/or the thickness of the filament yarn.

2. Because the filament yarn in a tangled condition is pressed into the needle holder 10 with the aid of the filter retainer which is externally shaped conformingly to the external peripheral surface of the body portion 12 of the former and because the needle holder 10 and the filter retainer 24 are longitudinally held in strict alignment with each other when being assembled together, the tangle 88 of the filament yarn can be easily and accurately fitted to the needle holder 10 simply by the reciprocating motions of the piston 90 in the transport tube 36.

3. Because the filament yarn 76 to form the filter element 22 is once elongated under tension and is allowed to shrink when released from the tension, the cut segment of the filament yarn has a tendency to curl and entwine on itself so that the filament element 22 constituted by the wad of the resultant filament yarn has a uniform density or, in otherwords, interstices which are distributed uniformly throughout the wad.

4. The external geomatry of the filter retainer 24 and accordingly the internal space of the needle holder 10 can be selected without respect to the side of the syringe barrel of a hypodermic syringe or the adapter of a venoclysis equipment to which the needle holder assembly according to the present invention is to be filled. This means that the space to accomodate the filter element 22 within the needle holder 10 can be selected irrespective of the size of the syringe barrel or the adapter of the venoclysis equipment.

5. Because of the fact that the filter element 22 is held in position within the needle holder 10 by means of the filter retainer 24 which is closely fitted to the needle holder 10 and which thus forms part of the needle holder assembly, the filter element 22 will not constitute an obstacle when the needle holder assembly is being fitted to a syringe barrel or an adapter of venocylsis equipment.

While a few embodiments of the medical needle holder assembly and only one embodiment of the apparatus according to the present invention have been described with reference to the accompanying drawings, it should be borne in mind that such are not limitative of the present invention and may therefore be changed and modified if desired without departing from the spirit and scope of the present invention.

What is claimed is:

1. Apparatus for assembling together a generally tubular needle holder, a filter element composed of a was of a predetermined length of filament yarn and a generally tubular filter retainer adapted to be received in said needle holder with said filter element fitter to the needle holder, comprising (1) an elongated hollow transport tube having a longitudinal passageway which is open at its foremost end and having formed in its intermediate portion an opening which is sized to permit said filament yarn to pass therethrough, (2) first feeding and positioning means for feeding said needle holder in each cycle of operation into a predetermined position longitudinally aligned with said longitudinal passageway in said transport tube and having its rearmost end located at the open foremost end of said longitudinal passageway, (3) second feeding and positioning means for feeding said filter retainer in each cycle of operation into a predetermined postion within said longitudinal passageway in said transport tube, said predetermined position of the filter retainer being longitudinally spaced apart and aligned with said predetermined position of said needle holder across said intermediate portion of said longitudinal passageway, (4) third feeding and positioning means for feeding said filament yarn in each cycle of operation into a predetermined position in said intermediate portion of said longitudinal passageway of said transport tube through said opening formed in the intermediate portion, (5) pneumatic transfer means for producing in said longitudinal passageway in said transport tube a unidirectional stream of air flowing from said intermediate portion toward said predetermined position of said filter retainer for moving said filament yarn from said predetermined position thereof toward said filter retainer in said predetermined position thereof until the filter element is forced in the form of a tangle against the foremost end of the filter retainer, and (6) drive means for moving said filter retainer from said predetermined position thereof toward said needle holder in said predetermined position thereof with said tangle of said filament yarn carried on the foremost end of the filter retainer and forcing the filter retainer into said needle holder in said predetermined position thereof so that the tangle of the filament yarn is compacted into wad form within said needle holder.

2. Apparatus as set forth in claim 1, in which said transport tube extends substantially horizontally.

3. Apparatus as set forth in claim 2, in which said first feeding and positioning means comprise a magazine formed with a vertical chamber having a bottom portion contiguous to and in line with the open foremost end of said longitudinal passageway in said transport tube, said magazine being adapted to accommodate within said vertical chamber a stack of needle holders each constituting said needle holder and said bottom portion of said vertical chamber providing said predetermined position of said needle holder, and a mechanism which is operative in predetermined cycles to downwardly convey said needle holders within said vertical chamber for successively positioning said needle holders in said bottom portion of said vertical chamber and to successively withdraw completed needle holder assemblies from said vertical chamber.

4. Apparatus as set forth in claim 2, in which said second feeding and positioning means comprise a magazine formed with a vertical chamber having a bottom end open to a rearmost portion of said longitudinal passageway in said transport tube, said magazine being adapted to accommodate within said vertical chamber a stack of filter retainers each constituting said filter retainer, said rearmost portion of said longitudinal passageway providing said predetermined position of said filter retainer, and a mechanism which is operative in predetermined cycles to downwardly convey said filter retainers successively into said rearmost portion of said longitudinal passageway in said transport tube.

5. Apparatus as set forth in claim 2, in which said opening is formed in a top wall of said intermediate portion of said transport tube and in which said third feeding and positioning means comprise a pair of feed rollers which are in rolling contact with each other above said opening in said intermediate portion of said transport tube, one of said feed rollers being driven from rotation by drive means for passing between the rollers a continuous filament yarn from a supply package, a tensioning roller located between said supply package and the set of said feed rollers for subjecting said continuous filament yarn to a predetermined tensile pull while the continuous filament yarn is being fed from said supply package toward said feed rollers, and cutting means located below said feed rollers for cutting said continuous filament yarn in said predetermined length in each cycle of operation, the predetermined length of filament yarn being admitted into said intermediate portion of said transport tube through said opening formed in said intermediate portion.

6. Apparatus as set forth in claim 5, in which said third feeding and positioning means further comprise a knife-edged member located between said tensioning roller annd said set of feed rollers and having a substantially horizontal sharpened edge for scraping thereagainst the continuous filament yarn being passed from said tensioning roller toward said feed rollers.

7. Apparatus as set forth in claim 6, in which said horizontal sharpened edge of said knife-edge member is located over and vertically in alignment with said opening in said intermediate portion of said transport tube.

8. Apparatus as set forth in claim 5, in which said third feeding and positioning means comprise a guide tube projecting upwardly from said top wall of said intermediate portion of said transport tube and formed with a vertical passageway extending from said opening and open at the upper end of said guide tube, said feed rollers being in rolling contact above said upper end of said guide tube.

9. Apparatus as set forth in claim 1, in which said drive means comprise a piston longitudinally movable through said longitudinal passageway in said transport tube between a first position having its foremost end engageable with the rearmost end of said filter retainer in said predetermined position thereof and a second position having said foremost end at the open foremost end of said longitudinal passageway in said transport tube and a mechanical driving mechanism connected to said piston for driving the piston to move between said first and second positions during each cycle of operation.

10. Apparatus as set forth in claim 9, in which said pneumatic transfer means comprise a source of suction, and passage means providing communication between said source of suction and the interior of said filter retainer in said predetermined position thereof.

11. Apparatus as set forth in claim 10, in which said passage means are constituted by a cavity formed in said piston and open at the foremost end of the piston, an aperture formed in the peripheral wall of the piston and open to said cavity, a vent formed in said transport tube and located to be in alignment with said aperture in said piston when said piston is in said first position thereof, and a passageway providing communication between said source of suction and sad vent.

* * * * *